United States Patent [19]

Gosteli

[11] 4,213,920
[45] Jul. 22, 1980

[54] PROCESS FOR THE PRODUCTION OF SUBSTITUTED BENZALDEHYDES

[75] Inventor: Jacques Gosteli, Basel, Switzerland

[73] Assignee: Ciba-Geigy Corporation, Ardsley, N.Y.

[21] Appl. No.: 920,102

[22] Filed: Jun. 28, 1978

[30] Foreign Application Priority Data

Jul. 6, 1977 [CH] Switzerland ............ 8338/77

[51] Int. Cl.$^2$ ............................................ C07C 45/00
[52] U.S. Cl. .................... 568/424; 260/465 R; 260/465 G; 260/465 K; 204/163 R; 568/655; 568/430
[58] Field of Search .......... 260/612 D, 600 R, 599, 260/465 G, 465 K, 465 R; 568/655

[56] References Cited

U.S. PATENT DOCUMENTS

| | | | |
|---|---|---|---|
| 3,067,205 | 12/1962 | Callighan et al. ............. | 260/599 X |
| 3,145,232 | 8/1964 | Thompson ..................... | 260/599 X |
| 3,637,721 | 1/1972 | Pappas et al. ................. | 260/599 X |
| 3,799,940 | 3/1974 | Mains ........................... | 260/599 X |

OTHER PUBLICATIONS

Kochergin et al., Chemical Abstracts vol. 58 [1963] 8942(b).
Morrison et al., Organic Chemistry, 3rd ed. (1973), 156–159.
Kliegl, Berichte, vol. 40 (#4) (1907) 4937–4942.

*Primary Examiner*—Bernard Helfin
*Attorney, Agent, or Firm*—Prabodh I. Almaula

[57] ABSTRACT

A process for the production of benzaldehydes which are substituted in the ortho-position by an electrophilic group R, which comprises brominating an ortho-substituted compound of the formula I

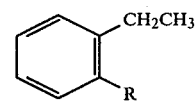

in which R represents the nitro group, the cyano group, an alkoxy group of 1 to 8 carbon atoms or a halogen atom, under irradiation with visible light in an inert solvent, to give the bromide of the formula II

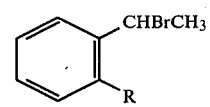

converting the resulting bromide by treatment with an alkali bromide in an inert solvent into a styrene compound of the formula III

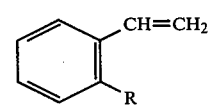

and ozonising this latter compound in an inert solvent to give the compound of the formula IV

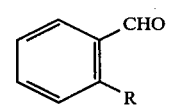

6 Claims, No Drawings

PROCESS FOR THE PRODUCTION OF SUBSTITUTED BENZALDEHYDES

It is known that benzaldehydes which contain in the ortho-position an electrophilic substituent are exceptionally difficult to obtain.

Although for example o-nitrobenzaldehyde has long been classed among the known substances and has been produced industrially, there still exists no advantageous synthesis for the manufacture of this compound at the present time. In general, o-nitrobenzaldehyde is described as difficult to obtain and whilst numerous existing patent specifications, for example German patent No. 48,722 (1889) or Japanese patent No. 307097 (1959), and publications, for example H. Cassebaum, J. Prakt. Chemie, 4. Reihe, vol. 29, 1965, relate to the manufacture of this aldehyde, the particulars provided are very incomplete. Even the method described in Org. Synth., Coll. Vol. III, 641, provides the aldehyde in a modest yield of 18%, starting from o-nitrotoluene.

The invention provides a process for the production of benzaldehydes which contain in the ortho-position an electrophilic radical R using correspondingly substituted o-ethyl benzene compounds as starting materials. An electrophilic substituent R is in particular the nitro group, and also the cyano group or a halogen atom, for example a chlorine, bromine, iodine or fluorine atom, as well as an alkoxy group of 1 to 8 carbon atoms.

The process of the present invention consists in brominating an ortho-substituted compound of the formula I

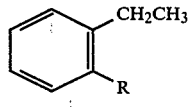

(I)

wherein R represents an electrophilic substituent, under irradiation with visible light (range: 3800–8000 Å), for example with the light of a tungsten lamp (incandescent lamp), in an inert solvent, in particular in the presence of a halogenated hydrocarbon, for example carbon tetrachloride or hexachloroethane, to give the bromide of the formula II

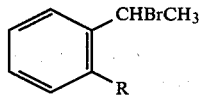

(II)

converting the resulting bromide by treatment with an alkali bromide, in particular sodium bromide, in an inert solvent, preferably a tertiary phosphoric acid amide, into a styrene compound of the formula III

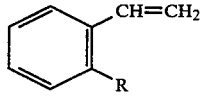

(III)

which is substituted in the ortho-position by an electrophilic group, and ozonising this latter compound in an inert solvent to give the compound of the formula IV

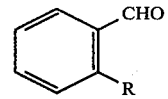

(IV)

The invention relates to a succession of process steps which lead from a unitary starting material, an ethyl benzene compound which is substituted in the ortho-position by an electrophilic group, via intermediates to give a pure end product. The treatment of o-nitrotoluene with bromine under irradiation with visible light, described by John R. Sampey et al., J. Am. Chem. Soc., 62, 1839 (1940), results in a bromination of the side-chain which proceeds in exceedingly low yield. H. Cassebaum, Zschr. f. Chemie, 9, 340 (1969), uses catalytic UV irradiation for the side-chain bromination of toluene, resulting in a relatively modest yield of, for example, o-nitrobenzyl bromide and a relatively large amount of unreacted o-nitrotoluene. Surprisingly, the side-chain bromination of the ethyl group according to the present invention at temperatures from 30° to 90° C., preferably from 40° to 60° C., results in an excellent, virtually quantitative, yield of an α-bromoethylbenzene which is substituted in the ortho-position. Under relatively mild reaction conditions, namely at temperatures between 60° and 120° C., preferably between 70° and 100° C., using an alkali bromide, especially sodium or potassium bromide, in an inert solvent, such as a tertiary phosphoric acid amide, preferably hexamethylphosphoric acid triamide, as reaction medium, this compound splits off hydrogen bromide to form ortho-substituted styrene. The styrene is oxidised to the ortho-substituted benzaldehyde with ozone-enriched oxygen at low temperatures from about −30° to +10° C., preferably from −20° to 0° C., in an inert solvent, for example a lower halogenated hydrocarbon, an alcohol or ester. Excess ozone or resulting ozone compounds are then advantageously selectively reduced with those conventional reducing agents which do not attack the nitro group, for example dimethyl sulphide or sodium bisulphite solutions.

Among the described process steps, special mention may be again made of the side-chain bromination of the o-nitroethyl benzene. The bromination of the homologous o-nitrotoluene is described as difficult to carry out in visible light by John R. Sampey et al. (op. cit.). The method described by H. Cassebaum (op. cit.) for the bromination of nitrotoluene having a similar structure results on the other hand, when irradiating with light in the UV range, in the formation of a dibromide in the side-chain with a low conversion rate and also partially in nuclear bromination. In addition, it has also been established that, for example, the bromides formed during the reaction decompose in the UV range, i.e. they are photolabile, thus preventing a high yield. It is therefore all the more surprising that, in spite of the negative opinions expressed on the use of o-nitrotoluene, the use of o-nitroethyl benzene results not only in a unitary bromination product, but also in a quantitative bromination.

The bromination of the present invention is carried out with elementary bromine under irradiation with visible light, i.e. in the range of 3800 to 8000 Å, in an inert solvent, especially in the presence of a halogenated hydrocarbon, for example carbon tetrachloride or hexachlorethane, in the temperature range between 30° and 90° especially between 40° and 60° C. Suitable sources of light for the process of the invention are tungsten lamps, for example incandescent filaments or fluorescent tubes, with which glass vessels can be irradiated externally, or immersion lamps for visible light, which can be built into metallic reaction vessels, are used. In order to prevent losses of light and heat in glass vessels, it is advantageous to provide a jacket of aluminum foil which reflects light. However, other sources of light can also be used, for example mercury vapour lamps, sodium vapour lamps etc.

The dehydrobromination of the ortho-substituted 2--bromoethyl benzene of the formula II to give the ortho-substituted styrene of the formula III is carried out in an inert solvent at relatively low temperatures between 60° and 120° C., preferably 70° and 100° C., with the aid of an alkali bromide.

Suitable inert solvents for this reaction are in particular tertiary phosphoric acid amides, for example hexamethylphosphoric acid triamide. Alkali bromides are in particular sodium and potassium bromide.

The oxidation of the styrene compound of the formula III to give the ortho-substituted benzaldehyde of the formula IV is effected according to the process of the invention by ozonisation at low temperature in the range from −30° to +10° C., especially from −20° to 0° C., in an inert solvent as reaction medium, with the aid of ozone-enriched Suitable inert solvents for this reaction are in particular the low-boiling chlorinated hydrocarbons, for example methylene chloride or chloroform, or alcohols, for example lower alkanols, such as methanol, or esters, for example ethyl acetate.

As examples of ortho-substituted ethyl benzenes which according to the present invention can be reacted to give ortho-substituted benzaldehydes there may be mentioned: o-cyanoethyl benzene, o-chloroethyl benzene, o-fluoroethyl benzene, o-methoxyethyl and o-ethoxyethyl benzene. In particular, however, an ortho-substituted ethyl benzene is o-nitroethyl benzene.

Compared with the closest prior art, i.e. in comparison with the process described by K. Liegl, Ber., Vol. 40, 4939 (1907), the ortho-substituted benzaldehyde is obtained by the novel process of the invention in high yield and without significant impurities.

o-Nitrobenzaldehyde can be used for example for the indigo synthesis of A.v. Baeyer. It is also used as a diagnostic agent in medicine, for example in diabetes. The correspondingly prepared o-cyanobenzaldehyde can be used as intermediate for obtaining anti-hypertensive pharmaceutical preparations with coronary dilating and peripherally dilating action (cf. German Offenlegungsschrift No. 1,963,188) and as starting material for the production of o-cyanocinnamic acids which are important for pharmaceutical syntheses. In addition, o-cyanobenzaldehyde is used for example as a stabilising additive for methyl chloroform (cf. U.S. Pat. No. 3,364,270) and as an additive for fibres containing polyvinyl alcohol to improve their elasticity and dyeability (cf. U.S. Pat. No. 3,071,429).

The invention is illustrated by the following Example.

EXAMPLE

A solution of 30.2 g of o-nitroethyl benzene in 400 ml of carbon tetrachloride and 10.8 ml of bromine is stirred and simultaneously irradiated (externally) with a 200 watt tungsten lamp. The temperature of the solution is 45° to 50° C. The smooth reaction course, accompanied by the evolution of hydrogen bromide, is complete after 1 hour. Solvent and excess bromine are stripped off in vacuo. The residual oil crystallises in a refrigerator and analysis shows it to be pure.

Yield: 46 g of o-nitro-α-bromoethyl benzene, corresponding to 100% of theory. Melting point: ~15°-20° C.

A mixture of 31.8 g of o-nitro-α-bromoethyl benzene, 38.2 g of sodium bromide and 400 ml of hexamethylphosphoric acid triamide is stirred for 16 hours at 80° C. After the mixture has cooled, it is diluted with 4 parts by volume of water and extracted with four 300 ml portions of ether. The combined organic layers are washed with water until the washings run colourless, dried over sodium sulphate and concentrated in vacuo, affording 20 g of a yellow oil as crude product. Elution with benzene through a column of 160 g of silica gel affords 18.8 g of pure o-nitrostyrene. Yield: 91% of theory.

Oxygen enriched with 10 m-moles of ozone are introduced at −20° C. in the course of 15 minutes into a solution of 1.50 g of o-nitrostyrene in 160 ml of methylene chloride. The faintly blue solution is scavenged with nitrogen until the colour has disappeared, treated with 10 ml of dimethyl sulphide and left to stand overnight at room temperature. The clear solution is concentrated in vacuo and the residue is taken up in ethyl acetate. The ethyl acetate solution is washed with water and sodium chloride solution, dried over sodium sulphate and concentrated. The crude product (1.75 g) is taken up in benzene and the solution is chromatographed through a column of silica gel (15 g). The first 100 ml of eluate are concentrated in vacuo, affording 1.39 g of pure o-nitrobenzaldehyde. Yield: 91.5% of theory.

What is claimed is:

1. A process for the production of benzaldehydes which are substituted in the ortho-position by an electrophilic group R, which comprises brominating an ortho-substituted compound of the formula I with elementary bromine

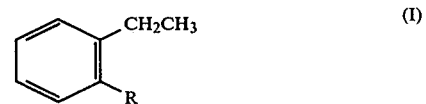

in which R represents the nitro group, the cyano group, an alkoxy group of 1 to 8 carbon atoms or a halogen atom, under irradiation with visible light in an inert halogenated hydrocarbon solvent, at a temperature between 30° and 90° C. to give the bromide of the formula II

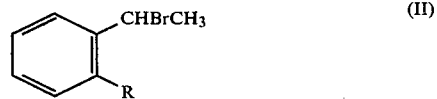

converting the resulting bromide at a temperature between 60° and 120° C. by treatment with an alkali bromide in an inert solvent other than that used above, into a styrene compound of the formula III

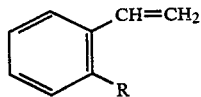 (III)

and ozonising this latter compound in an inert solvent to give the compound of the formula IV

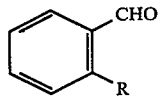 (IV)

2. A process according to claim 1, wherein a tertiary phosphoric acid amide is used an inert solvent, when converting the bromide into a styrene compound.

3. A process according to claim 2, wherein hexamethylphosphoric acid triamide is used as inert solvent.

4. A process according to claim 1, wherein the resulting ortho-substituted styrene of the formula III is reacted with ozone-enriched oxygen at a temperature between 31 30° and +10° C. in an inert solvent to give the ortho-substituted benzaldehyde of the formula IV.

5. A process according to claim 4, wherein a low-boiling chlorinated hydrocarbon, a lower alkanol or an ester is used as inert solvent.

6. A process according to claim 1, wherein o-nitroethyl benzene is reacted to give o-nitrobenzaldehyde.

* * * * *

UNITED STATES PATENT AND TRADEMARK OFFICE
CERTIFICATE OF CORRECTION

PATENT NO. : 4,213,920

DATED : July 22, 1980

INVENTOR(S) : Jacques Gosteli

It is certified that error appears in the above—identified patent and that said Letters Patent are hereby corrected as shown below:

Title page"[73] Assignee: Ciba-Geigy Corporation, Ardsley, N.Y." should be deleted.

Signed and Sealed this

Twenty-first Day of October 1980

[SEAL]

Attest:

SIDNEY A. DIAMOND

Attesting Officer

Commissioner of Patents and Trademarks